United States Patent [19]

Ward

[11] Patent Number: 4,568,377
[45] Date of Patent: Feb. 4, 1986

[54] HERBICIDAL 5-AMINO-3-OXO-4-(SUBSTITUTED-PHENYL)-2,3-DIHYDROFURAN

[75] Inventor: Carl E. Ward, San Jose, Calif.

[73] Assignee: Chevron Research Company, San Francisco, Calif.

[21] Appl. No.: 727,459

[22] Filed: Apr. 26, 1985

[51] Int. Cl.$^4$ .................. A01N 43/08; C07D 307/66
[52] U.S. Cl. ............................. 71/88; 546/214; 546/283; 548/517; 549/479; 71/94; 71/95; 71/76
[58] Field of Search .............. 549/479; 71/88, 94, 71/95; 546/205, 206, 214, 283; 548/517

[56] References Cited
U.S. PATENT DOCUMENTS 4,441,910 4/1984 Shapiro ............................. 71/90
4,537,623 8/1985 Ward ............................. 549/472 X

FOREIGN PATENT DOCUMENTS 42-19090 9/1967 Japan .
44-13710 6/1969 Japan .
1521092 8/1978 United Kingdom .
2080289 2/1982 United Kingdom .

OTHER PUBLICATIONS

Meier et al, Chemical Abstracts, vol. 94 (1981) 138818v.
Capraro et al, Helvetica Chmica Acta—vol. 66, Fasc. 1 (1983)–No. 31, pp. 362–378.
Umio, et al, Chem. Abstracts, vol. 70, 1969, 68123t.
Volovenko et al; Chem. Abstracts, vol. 95, 1981, 24799e.

Primary Examiner—Richard L. Raymond
Attorney, Agent, or Firm—T. G. DeJonghe; L. S. Squires

[57] ABSTRACT

5-Amino-2-aryl-3-oxo-4-(substituted-phenyl)-2,3-dihydrofuran and derivatives thereof. The compounds generally exhibit both pre-emergence and post-emergence phytotoxicity with respect to grassy and broadleaf weeds and have improved crop safety.

29 Claims, No Drawings

HERBICIDAL 5-AMINO-3-OXO-4-(SUBSTITUTED-PHENYL)-2,3-DIHYDROFURAN

BACKGROUND OF THE INVENTION

This invention relates to 5-amino-3-oxo-4-(substituted-phenyl)-2,3-dihydrofuran derivatives and to the use of such compounds as herbicides and plant growth regulators.

Chemiker-*Zeitung* 104 (1980) No. 10, Pages 302-303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application 13,710/69 (Chemical Abstracts 71:61195e) discloses the generic formula for 5-amino-3-oxo-4-(phenyl and halophenyl)-2,3-dihydrofuran and specifically discloses 5-amino-3-oxo-4-(phenyl and 4-chlorophenyl)-2,3-dihydrofurans. Japanese Pat. No. 19090 (Chemical Abstracts 69P10352e) discloses certain 2,3-dihydrothiophenes as pharmaceuticals. *Helvetica Chemica Acta,* Volume 66, Pages 362-378 (1983) discloses 5-N-cyclopropyl-4-phenyl-2-methoxycarbonylmethylene-3-furanone as part of an academic chemical synthesis discussion. U.S. Pat. No. 4,441,910 discloses herbicidal ureidosulfonylfurans and ureidosulfonylthiophenes.

My copending U.S. application Ser. Nos. 607,610, filed May 9, 1984, and now abandoned, and 666,075, filed Oct. 26, 1984 and 684,997 disclose and claim certain 2-substituted-5-amino and substituted amino-3-oxo-4-substituted phenyl-2,3-dihydrofuran derivatives having herbicidal activity. My copending U.S. application Ser. No. 623,805, filed June 22, 1984, discloses and claims certain 2-substituted-5-amino and substituted amino-3-oxo-4-substituted phenyl-2,3-dihydrothiophene herbicides.

SUMMARY OF THE INVENTION

I have now discovered certain analogs of the compounds described in my previous application, U.S. Ser. No. 607,610, filed May 9, 1984, and now abandoned, which also exhibit pre-emergence and post-emergence herbicidal activity and have improved crop safety, especially with respect to soybean. At lower application rates the compounds exhibit plant growth regulating properties.

The compounds of the present invention can be represented by the following formula:

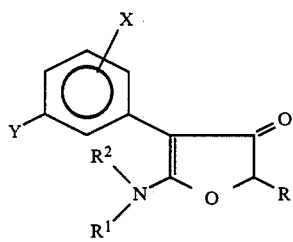

(I)

wherein

R is phenyl, naphth-1-yl, inden-1-yl; 4-fluorophenyl; or substituted aryl selected from the group having the formulas:

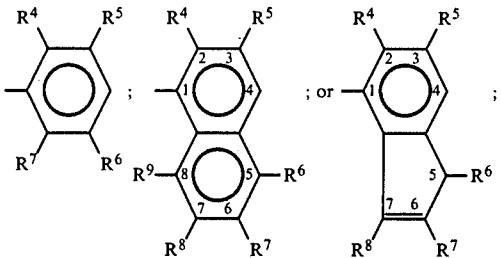

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen;

$R^1$ is hydrogen or alkyl having 1 through 4 carbon atoms;

$R^2$ is hydrogen, alkyl having 1 through 4 carbon atoms, cycloalkyl having 3 through 7 carbon atoms, alkenyl having 3 or 4 carbon atoms, alkoxycarbonylalkyl having from 1 through 4 carbon atoms in the alkoxy moiety and from 1 through 4 carbon atoms in the alkyl moiety alkoxyalkyl wherein the alkoxy and alkyl moieties independently have 1 through 3 carbon atoms or alkylthioalkyl wherein the alkyl moieties independently have 1 through 3 carbon atoms; or $R^1$ and $R^2$ together with the nitrogen to which they are joined form a saturated or unsaturated nitrogen heterocycle having from 5 or 6 ring atoms one of which is nitrogen and the remainder of which are carbon atoms;

X is hydrogen, lower alkyl, lower alkoxy, halo, trifluoromethyl and can be at any available position on the phenyl ring; and Y is cyano, nitro, alkoxycarbonyl having 2 through 9 carbon atoms; cyclopentyloxycarbonyl; cyclohexyloxycarbonyl; phenoxycarbonyl; substituted phenoxycarbonyl having one or two substituents independently selected from the group of lower alkyl having 1 through 6 carbon atoms, lower alkoxy having 1 through 6 carbon atoms, halo, haloalkyl having 1 through 3 carbon atoms and 1 through 4 of the same or different halo atoms, nitro or cyano; alkylthiocarbonyl having 2 through 9 carbon atoms or

wherein $R^{10}$ and $R^{11}$ are independently hydrogen or alkyl having 1 through 8 carbon atoms; with the proviso that when X is other than hydrogen and $R^1$ and $R^2$ are each hydrogen then R must be methyl, ethyl, propyl, 2-halophenyl, 2-lower alkylphenyl or 4-fluorophenyl.

The invention also comprises compatible salts of the compound of Formula (I), for example, acid addition salts with respect to the exocyclic amino group; and salts obtained via replacement of the exocyclic amino hydrogen (i.e., $R^1$ and $R^2$ is hydrogen) with a compatible cation or enolation of the 3-oxo group following replacement of the amino hydrogen.

The compounds of Formula (I) exist as keto ⇌ enol isomers. The compounds also have an asymmetric carbon atom and can also exist as optical isomers. In some instances the compounds also exist as geometric isomers. The above formula is intended to encompass the respective individual isomers as well as mixtures thereof and the respective isomers as well as mixtures thereof are encompassed within the invention.

It has also been discovered that the presence of a 3-trifluoromethyl substituent on the 4-phenyl group of the compounds of the present invention generally very substantially enhances herbicidal activity.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 2, 3, 6–10 set forth hereinbelow on Pages 24–30 and 33–51. In terms of substituents, the preferred compounds are those wherein R is phenyl or substituted phenyl, preferably phenyl, monomethylphenyl or monohalophenyl, and especially 2-halophenyl, 2-lower alkylphenyl, or 4-fluorophenyl; $R^1$ and $R^2$ are independently hydrogen, methyl, ethyl or n-propyl, and more preferably one of $R^1$ or $R^2$ is hydrogen and the other is methyl, ethyl or n-propyl, preferably hydrogen, methyl or ethyl, especially methyl; X is hydrogen; and Y is alkoxycarbonyl, cyclopentylcarbony, cyclohexylcarbonyl, cyano or nitro, more preferably alkoxycarbonyl, especially methoxycarbonyl, trifluoromethyl. Most preferably the compounds contain a combination of two or more preferred substituents. The compounds of Formula (I) wherein $R^1$ and $R^2$ are each hydrogen generally exhibit poor herbicidal activity but are very useful as intermediates to prepare the preferred $R^2$ is methyl, ethyl or propyl herbicidal compounds of the invention.

The compounds of Formula (I) wherein $R^1$ and $R^2$ are each hydrogen and hydrohalide addition salts thereof, can be conveniently prepared by the following schematically represented process:

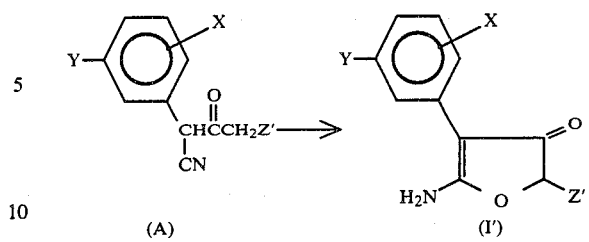

wherein
X and Y are as defined hereinabove; and
Z' is aryl, or substituted aryl.

Rearrangement of Compound (A) to Compound (I') can be conveniently effected by contacting Compound (A) with a halogen, preferably bromine, and water and optionally a liquid carboxylic acid in the presence of an inert organic solvent.

Typically, this process is conducted at temperatures in the range of about from 0° to 100° C., preferably about from 20° to 30° C., for about from 4 to 36 hours, preferably about from 18 to 24 hours, using about from 1.0 to 10.0, preferably 1.0 to 1.1 moles of halogen per mole of Compound (A). Suitable liquid carboxylic acids which can be used include, for example, acetic acid, propionic acid, butyric acid, formic acid, and the like. By using excess carboxylic acid, the excess can serve as solvent or liquid carrier for this reaction system. Other organic solvents which can be used include, for example, liquid halogenated alkanes, for example, methylene chloride, carbon tetrachloride, chloroform, 1,2-dichloroethane; liquid aromatics, for example, benzene, toluene; liquid alkyl ethers, for example, diethylether, dimethyl, sulfoxide, dimethylforamide, and the like, and compatible mixtures thereof.

Best results are obtained using bromine as the halogen, although chlorine and iodine could also be used. Also, by using additional hydrohalide the corresponding hydrohalide addition salt of the compound of Formula (I') may be retained.

The starting materials of Formula (A) can be prepared by the following schematically represented process:

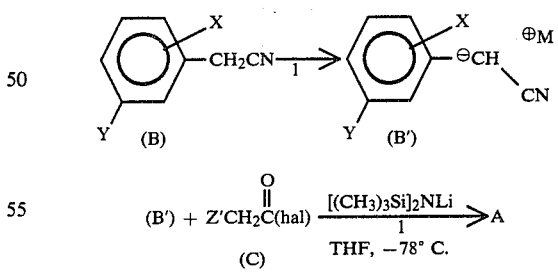

wherein
(hal) is chloride or bromide; and
Z', Y and X are as defined hereinabove and
$M^\oplus$ is an alkali metal cation, preferably $Li^\oplus$.

This process can be conveniently effected by contacting Compound (B) with Compound (C), and a strong base, preferably in an inert organic solvent.

Although this process is schematically shown as two steps, the second step is typically and conveniently conducted in situ with the reaction product mixture of the first step. Also, as is conventional with such reactions, the reactions are preferably conducted under anhydrous conditions under an inert gas (e.g., nitrogen).

In the first step of this process Compound (B) is contacted with a non-nucleophilic base, preferably in an inert organic solvent. This step is typically conducted at temperatures in the range of about from −78° to −30° C. for about from ½ to 3 hours using about from 1 to 2, preferably about 2 to 2.1, mole equivalents of non-nucleophilic base per mole of Compound (B). Suitable non-nucleophilic bases which can be used include, for example, alkali metal hydrides, e.g., sodium hydride, potassium hydride, etc.; alkali metal amides, e.g., lithium bis(trimethylsilyl)amide; sodium bis(trimethylsilyl)amide; potassium bis(trimethylsilyl)amide; lithium diethylamide, lithium diisopropyl amide; sodium dimethylamide, and the like. Lithium bis(trimethyl-silyl)amide is generally preferred as it has given very good results and is readily commercially available. The alkali metal amides, and also of course the alkali metal hydrides, are generally known compounds and can be prepared by known procedures, or obvious modifications thereof. For example, the alkali metal amides can be prepared by the reaction of a secondary amine with an alkyl alkali metal.

Suitable inert organic solvents, which can be used, include, for example, tetrahydrofuran, dioxane, dimethoxyethane, diethyl ether, diisopropyl ether, and the like and compatible mixtures thereof.

The second step can be effected by contacting Compound (B') with the appropriate substituted acetyl halide (C) having the desired Z' group, preferably in an inert organic solvent. As noted above, this step is conveniently conducted in situ with the reaction product mixture of the first step.

This step is typically conducted at temperatures in the range of about from −78° to −30° C., preferably −78° to −50° C. for about from 1 to 18 hours, preferably 1 to 5 hours using about from 1 to 1.5 moles, preferably 1 to 1.1 moles of Compound (C) per mole of Compound (B'). Suitable inert organic solvents include those given above with respect to the first step of this process, and the like.

The starting materials of Formulas (B) and (C) are generally known materials and can be prepared by known procedures, or obvious modifications thereof (i.e., substitution of appropriate starting materials). The preparation of Compound (B) is for example described in Org. Syn. Coll., Volume 1, 107 (1941), and a method useful for preparation of Compound (C) is described in Org. Syn. Coll., Volume 4, 715 (1963).

The compound of Formula (I) wherein one or both of $R^1$ and $R^2$ are substituted can be prepared by alkylation of the amino group of the corresponding compounds of formula I":

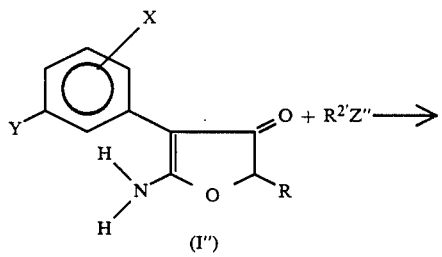

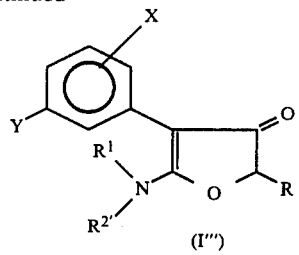

wherein
R, $R^1$, X and Y are as defined hereinabove; and
$R^{2'}$ is as defined for $R^2$ but is not hydrogen; and
$R^{2'}Z''$ is an alkylation agent having the appropriate $R^{2'}$ or appropriate $R^1$ group if dialkylation is desired.

This process can be effected by contacting Compound (I") with a suitable alkylation agent capable of alkylating primary or secondary amino groups.

For example, this can be effected by contacting Compound (I") with $R^{2'}$ iodide or bromide, preferably in an inert organic solvent and preferably in the presence of a scavenger base. Typically, this process is conducted at temperatures in the range of about from 0° to 100° C., preferably 20° to 45° C. for about from 1.0 to 72.0, preferably 2.0 to 18.0 hours. Where it is desired to monoalkylate, then typically about from 1.0 to 1.1 moles of $R^{2'}$ halide reactant is used per mole of Compound (I"). Where it is desired to alkylate both amino hydrogens, then typically about from 1.9 to 4.0 moles of $R^{2'}$ halide are used per mole of Compound (I"). In the case where it is desired to prepare the compound wherein $R^{2'}$ is alkoxyalkyl or alkylthioalkyl, it is preferred to use a large excess of $R^{2'}$ halide even where monoalkylation is desired; for example 3 to 6 moles of $R^{2'}Z''$ per mole of I". Further alkylation can be effected in a second step if desired. Also variation in $R^1$ and $R^2$ can be effected by first alkylating only one of the two amino hydrogens and then alkylating the second amino hydrogen with an alkylating agent having a different $R^{2'}$ group. The compounds wherein $R^1$ and $R^2$ together with the amino nitrogen atoms form a saturated heterocycle can be prepared by using the appropriate $Z''$—$(CH_2)_{2-5}$—$Z'''$, wherein $Z''$ is Cl or Br alkylating agent. The $R^1R^2N$ unsaturated heterocycle can be prepared by using the appropriate cis-alkenyl dihalide, wherein one of the halo atoms is on each of the terminal alkenyl carbon. Suitable inert organic solvents which can be used, include, for example, liquid halogenated alkanes; for example, methylene chloride, carbon tetrachloride, or dichloroethane; also useful are tetrahydrofuran and the like. Suitable scavenger bases which can be used include, for example, the bases described hereinabove with respect to the reaction of Compound (B) with Compound (C).

The compounds of Formula (I''') wherein $R^1$ is lower alkyl (e.g. methyl) and $R^2$ is hydrogen or lower alkyl, are advantageously prepared using dialkyl sulfate as the alkylating agent. This can be conveniently effected by contacting the compound of Formula I wherein one or both of $R^1$ and/or $R^2$ are hydrogen with the desired lower alkyl sulfate in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound I. An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The compatible salts of Formula (I) can be prepared by conventional procedures for example by treating the compound of Formula (I) wherein $R^1$ and/or $R^2$ are hydrogen with a suitable strong base such as, for example, n-butyllithium, sodium hydride, potassium hydride, and the like, having the desired cation, by conventional procedures to yield the corresponding $R^1$ and/or $R^2$ cation salts. The enolate salts can be prepared by treating the $R^1$ and/or $R^2$ cation salts with base via conventional procedures. The acid addition salts can be prepared by reacting the compounds of Formula (I) with a strong acid, preferably under anhydrous condition. Suitable strong acids include, for example, hydrogen fluoride, hydrogen bromide, hydrogen chloride, hydrogen iodide, sulfuric acid and the like. Additional variations in the salt can also be effected via ion exchange with the appropriate ion exchange resin.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions would also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups and includes, for example, $-CH_2-$; $-CH_2-CH_2-$;

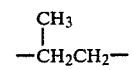

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group $-OR'$ wherein $R'$ is lower alkyl.

The term "lower alkylthio" refers to the group $-SR'$ wherein $R'$ is lower alkyl.

The term "lower alkoxyalkyl" refers to the group $R'OR''-$ wherein $R'$ and $R''$ are independently straight chain or branched chain alkyl groups having 1 through 3 carbon atoms.

The term "lower alkylthioalkyl" refers to the group $R'SR''-$ wherein $R'$ and $R''$ are independently straight chain or branched chain alkyl groups having 1 through 3 carbon atoms.

The term "lower alkoxycarbonylalkyl" refers to the group

wherein $R'$ is lower alkyl and $R''$ is alkylene having 1 through 4 carbon atoms and can be straight or branched chained. Typical alkoxycarbonylalkyl groups include for example, $-CH_2C(O)OCH_3$; $-CH(CH_3)C(O)OC_2H_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably and lower haloalkyl group has 1 or 2 carbon atoms.

The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substituted aryl groups include, for example, 2-fluorophenyl, 2-chlorophenyl, 2,6-dimethylphenyl, 4-fluorophenyl, 2-methylphenyl, 2-chloro,3-chloromethylphenyl, 2-nitro,5-methylphenyl, 2,6-dichlorophenyl, 3-trifluoromethylphenyl, 2-methoxyphenyl, 2-bromonaphth-1-yl, 3-methoxyinden-1-yl, and the like.

The term "arylalkylene" refers to the group $ArR^3-$ wherein Ar is aryl and $R^3$ is alkylene having 1 through 3 carbon atoms and includes both straight-chained and branched-chained alkylenes, for example, methylene, ethyl, 1-methylethyl, and propyl.

The term "saturated nitrogen heterocycle" as used herein with respect to $R^1$ and $R^2$ of formula I refers to the groups having the formula:

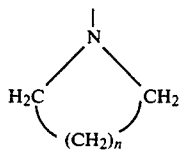

wherein
n is 2 or 3.

The term "unsaturated nitrogen heterocycle" as used herein with respect to $R^1$ and $R^2$ of formula I refer to the groups having the formulas:

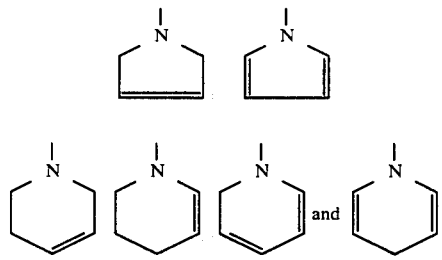

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20°–25° C.

Utility

The compounds of Formula (I) exhibit both pre-emergence and post-emergence herbicidal activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liqid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduces the leachability of the compound or otherwise enhance soil stability.

The composition can also contain various compatible adjuvants, stabilizers, conditioners, insecticides, fungicides, and if desired, other herbicidally active compounds.

At reduced dosages certain of the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volumes. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

Example 1

(3-Methoxycarbonyl)-benzylcarbonyl-acetonitrile

In this example a mixture containing 17.0 g of 3-methoxycarbonylphenylacetonitrile in 20 ml of tetrahydrofuran was added dropwise to 97 ml of a 1 molar solution of lithium bis(trimethylsilyl)amide under nitrogen at −78° C. The mixture was stirred for one hour at −78° C. and then 15 g of phenylacetyl chloride in 20 ml of tetrahydrofuran was added dropwise. The mixture was stirred for one hour at −78° C. and then allowed to warm to room temperature. The mixture was concentrated by evaporation under vacuum and then mixed with water and ethyl ether. The ether layer and aqueous layers were separated. The aqueous layer was extracted with ethyl ether. The ether extracts were combined with the ether layer. The extracted aqueous layer was added to saturated aqueous ammonium chloride and then again extracted with ethyl ether. The pH of the aqueous phase was then reduced to pH 4 with aqueous 10% wt hydrochloric acid and then extracted three more times with ethyl ether and washed with saturated aqueous sodium bicarbonate, dried over magnesium sulfate and evaporated yielding 8.0 g of a viscous oil. The ether layer was dried over magnesium sulfate and then concentrated by evaporation yielding 19.4 g of a gummy oil. The oils were combined and then chromatographed over silica eluting with 30%v ethyl acetate:70%v petroleum ethers. The product fractions were triturated in 50% vol ethyl ether:50% vol petroleum ether affording 8.1 g of the title compound as a solid.

Similarly, by adapting the above procedure using the appropriately substituted-phenyl acetonitrile and arylacyl chlorides starting materials, the following compounds can be prepared:

(5-chloro-3-methoxycarbonylphenyl)-benzylcarbonyl-acetonitrile;
(4-chloro-3-methoxycarbonylphenyl)-benzylcarbonyl-acetonitrile;
(2-bromo-3-methoxycarbonylphenyl)-benzylcarbonyl-acetonitrile;
(6-fluoro-3-methoxycarbonylphenyl)-benzylcarbonyl-acetonitrile;
(4-methyl-3-methoxycarbonylphenyl)-benzylcarbonyl-acetonitrile;
(5-methoxy-3-methoxycarbonylphenyl)-benzylcarbonyl-acetonitrile;
(6-methyl-3-methoxycarbonylphenyl)-benzylcarbonyl-acetonitrile;
(3-methoxycarbonyl-5-trifluoromethylphenyl)-benzylcarbonyl-acetonitrile;
(3-methoxycarbonyl-5-fluorophenyl)-benzylcarbonyl-acetonitrile;
(3-cyclopentyloxycarbonylphenyl)-benzylcarbonyl-acetonitrile;
(3-methoxycarbonylphenyl)-(4-fluorobenzylcarbonyl)-acetonitrile;
(3-methoxycarbonylphenyl)-1-naphthylmethylene-acetonitrile;
(2-chloro-3-phenoxycarbonylphenyl)-benzylcarbonyl-acetonitrile;
(4-ethyl-3-2',6'-dimethylphenoxycarbonylphenyl)-benzylcarbonyl-acetonitrile;
(5-methoxy-3-3',5'-dichlorophenoxycarbonylphenyl)-benzylcarbonyl-acetonitrile;
(3-3'-iodo-4'-methoxyphenoxycarbonylphenyl)-benzylcarbonyl-acetonitrile;
(3-2'-nitro-4'-trifluoromethylphenoxycarbonylphenyl)-benzylcarbonyl-acetonitrile;
(3-heptylthiocarbonylphenyl)-benzylcarbonyl-acetonitrile;
(3-cyclohexyloxycarbonylphenyl)-benzylcarbonyl-acetonitrile;
(3-cyanophenyl)-(2-nitrobenzylcarbonyl)-acetonitrile;
(2-chloro-3-nitrophenyl)-benzylcarbonyl-acetonitrile;
(3-ethylthiocarbonyl-2-ethylphenyl)-naphth-1-ylmethylenecarbonyl-acetonitrile;
(3-dimethylaminophenyl)-beta-naphth-1-ylmethylcarbonyl-acetonitrile;
(3-aminophenyl)-benzylcarbonyl-acetonitrile;
(3-methylaminophenyl)-benzylcarbonyl-acetonitrile;
(3-dioctylaminophenyl)-benzylcarbonyl-acetonitrile;
(3-propylthiocarbonylphenyl)-benzylcarbonyl-acetonitrile;
(3-2',5'-dimethoxyphenoxycarbonylphenyl)-benzylcarbonyl-acetonitrile;
(3-3',4'-dibromophenoxycarbonylphenyl)-(3-nitrobenzylcarbonyl)-acetonitrile;
(3-methoxycarbonylphenyl)-(2,3-dichlorobenzylcarbonyl)-acetonitrile;
(3-ethoxycarbonylphenyl)-1-naphthylmethylenecarbonyl-acetonitrile;
(3-propoxycarbonylphenyl)-(3-chloro-8-fluoronaphth-1-ylmethylenecarbonyl)-acetonitrile;
(3-isopropoxycarbonylphenyl)-[(2-trifluoromethyl-3-methyl-8-methoxy-napth-1-yl)methylenecarbonyl]-acetonitrile;
(3-butoxycarbonylphenyl)-(inden-1-ylmethylenecarbonyl)-acetonitrile; and
(3-hexoxycarbonylphenyl)-(2-fluoroinden-1-ylmethylenecarbonyl)-acetonitrile.

Example 2

2-Phenyl-3-oxo-4-(3-methoxycarbonylphenyl)-5-amino-2,3-dihydrofuran

In this example 0.4 g of water was admixed with 6.5 g of (3-methoxycarbonylphenyl)-benzylcarbonyl-acetonitrile in about 40 ml of methylene chloride at room temperature. 1.1 ml of bromine in about 10 ml of methylene chloride was added dropwise at room temperature. After addition of the bromine, the reaction mixture was mixed with saturated aqueous sodium bicarbonate and stirred for about ½ hour at room temperature, resulting in a two-phase liquid mixture. The phases were separated. The aqueous phase was extracted three times with methylene chloride. The combined extracts and methylene chloride phase were washed twice with saturated aqueous sodium bicarbonate, dried over magnesium sulfate and concentrated by evaporation affording an oily residue. The residue was triturated with a mixture of ethyl ether and petroleum ethers affording 5.0 g of the title compound as a solid.

Similarly, by adapting the above procedure to the compounds listed in Example 1, the following compounds can be prepared:

2-phenyl-3-oxo-4-(5-chloro-3-methoxycarbonylphenyl)-5-amino-2,3-dihydrofuran;
2-phenyl-3-oxo-4-(4-chloro-3-methoxycarbonylphenyl)-5-amino-2,3-dihydrofuran;
2-phenyl-3-oxo-4-(2-bromo-3-methoxycarbonylphenyl)-5-amino-2,3-dihydrofuran;
2-phenyl-3-oxo-4-(6-fluoro-3-methoxycarbonylphenyl)-5-amino-2,3-dihydrofuran;
2-phenyl-3-oxo-4-(4-methyl-3-methoxycarbonylphenyl)-5-amino-2,3-dihydrofuran;
2-phenyl-3-oxo-4-(5-methoxy-3-methoxycarbonylphenyl)-5-amino-2,3-dihydrofuran;
2-phenyl-3-oxo-4-(6-methyl-3-methoxycarbonylphenyl)-5-amino-2,3-dihydrofuran;
2-phenyl-3-oxo-4-(3-methoxycarbonyl-5-trifluoromethylphenyl)-5-amino-2,3-dihydrofuran;
2-phenyl-3-oxo-4-(3-ethoxycarbonyl-5-fluorophenyl)-5-amino-2,3-dihydrofuran;
2-phenyl-3-oxo-4-(3-cyclopentyloxycarbonylphenyl)-5-amino-2,3-dihydrofuran;
2-(4-fluorophenyl)-3-oxo-4-(3-methoxycarbonylphenyl)-5-amino-2,3-dihydrofuran;
2-(1-naphthyl)-3-oxo-4-(3-methoxycarbonylphenyl)-5-amino-2,3-dihydrofuran;
2-phenyl-3-oxo-4-(2-chloro-3-phenoxycarbonylphenyl)-5-amino-2,3-dihydrofuran;
2-phenyl-3-oxo-4-(4-ethyl-3-2',6'-dimethylphenoxycarbonylphenyl)-5-amino-2,3-dihydrofuran;
2-phenyl-3-oxo-4-(5-methoxy-3-3',5'-dichlorophenoxycarbonylphenyl)-5-amino-2,3-dihydrofuran;
2-phenyl-3-oxo-4-(3-3'iodo-4'-methoxyphenoxycarbonylphenyl)-5-amino-2,3-dihydrofuran;
2-phenyl-3-oxo-4-(3-2'-nitro-4'-trifluoromethylphenoxycarbonylphenyl)-5-amino-2,3-dihydrofuran;
2-phenyl-3-oxo-4-(3-heptylthiocarbonylphenyl)-5-amino-2,3-dihydrofuran;
2-phenyl-3-oxo-4-(3,5-cyclohexyloxyphenyl)-5-amino-2,3-dihydrofuran;
2-(2-nitrophenyl)-3-oxo-4-(3-cyanophenyl)-5-amino-2,3-dihydrofuran;
2-phenyl-3-oxo-4-(2-chloro-3-nitrophenyl)-5-amino-2,3-dihydrofuran;
2-(1-naphthyl)-3-oxo-4-(3-ethylthiocarbonyl-2-ethylphenyl)-5-amino-2,3-dihydrofuran;
2-(1-naphthyl)-3-oxo-4-(3-dimethylcarbamoylphenyl)-5-amino-2,3-dihydrofuran;
2-phenyl-3-oxo-4-(3-carbamoylphenyl)-5-amino-2,3-dihydrofuran;
2-phenyl-3-oxo-4-(3-methylcarbamoylphenyl)-5-amino-2,3-dihydrofuran;
2-phenyl-3-oxo-4-(3-dioctylaminophenyl)-5-amino-2,3-dihydrofuran;
2-phenyl-3-oxo-4-(3-propylthiocarbonylphenyl)-5-amino-2,3-dihydrofuran;
2-phenyl-3-oxo-4-(3-2',5'-dimethoxycarbonylphenyl)-5-amino-2,3-dihydrofuran;
2-(3-nitrophenyl)-3-oxo-4-(3-3',4'-dibromophenoxycarbonylphenyl)-5-amino-2,3-dihydrofuran;
2-(2,3-dichlorophenyl)-3-oxo-4-(3-methoxycarbonylphenyl)-5-amino-2,3-dihydrofuran;
2-(1-naphthyl)-3-oxo-4-(3-ethoxycarbonylphenyl)-5-amino-2,3-dihydrofuran;
2-(3-chloro-8-fluoronaphth-1-yl)-3-oxo-4-(3-propoxycarbonylphenyl)-5-amino-2,3-dihydrofuran;
2-(2-trifluoromethyl-3-methyl-8-methoxy-naphth-1-yl)-3-oxo-4-(3-isopropoxycarbonylphenyl)-5-amino-2,3-dihydrofuran;
2-inden-1-yl-3-oxo-4-(3-butoxycarbonylphenyl)-5-amino-2,3-dihydrofuran; and
2-(2-fluoroinden-1-yl)-3-oxo-4-(3-hexoxycarbonylphenyl)-5-amino-2,3-dihydrofuran.
2-(3-chlorophenyl)-3-oxo-4-(2-trifluoromethyl-3-dimethylcarbamoylphenyl)-5-amino-2,3-dihydrofuran;
2-naphth-1-yl-3-oxo-4-(5-trifluoromethyl-3-ethylthiocarbonylphenyl)-5-amino-2,3-dihydrofuran;
2-(3-methylphenyl)-3-oxo-4-(3-butoxycarbonyl-4-methylphenyl)-3-oxo-5-amino-2,3-dihydrofuran;
2-(3-fluorophenyl)-3-oxo-4-(3-3'-chlorophenoxycarbonylphenyl)-5-amino-2,3-dihydrofuran;
2-(2,3,5-trifluorophenyl)-3-oxo-4-(3-phenoxycarbonylphenyl)-5-amino-2,3-dihydrofuran;
2-(3-methylnapth-1-yl)-3-oxo-4-(3-methoxycarbonylphenyl)-5-amino-2,3-dihydrofuran.

EXAMPLE 3

2-Phenyl-3-oxo-4-(-3-methoxycarbonylphenyl)-5-methylamino-2,3-dihydrofuran

The title compound can be prepared via the following procedure.

In this example, 0.60 g of solid sodium hydroxide in 4.0 ml of water was added to a mixture of 4.1 g of 2-phenyl-3-oxo-4-(3-methoxycarbonylphenyl)-5-amino-2,3-dihydrofuran in 70 ml of methylene chloride at room temperature followed by the addition of 1.73 g of dimethyl sulfate and 0.30 g of benzyltriethyl ammonium chloride. The two-phase mixture was then stirred at room temperature for about 18 hours and then washed one time with water, dried over magnesium sulfate and then concentrated by evaporation under vacuum to yield an oil. The oil was triturated with 1:1 diethyl ether:methanol to afford 2.3 g of the title compound as a white powder.

Similarly, by adapting the above procedure using the other products listed in Example 2 as starting materials, the corresponding 5-methylamino homologs thereof can be prepared, for example:

2-phenyl-3-oxo-4-(5-chloro-3-methoxycarbonylphenyl)-5-methylamino-2,3-dihydrofuran;
2-phenyl-3-oxo-4-(4-chloro-3-methoxycarbonylphenyl)-5-methylamino-2,3-dihydrofuran;
2-phenyl-3-oxo-4-(2-bromo-3-methoxycarbonylphenyl)-5-methylamino-2,3-dihydrofuran;
2-phenyl-3-oxo-4-(6-fluoro-3-methoxycarbonylphenyl)-5-methylamino-2,3-dihydrofuran;
2-phenyl-3-oxo-4-(4-methyl-3-methoxycarbonylphenyl)-5-methylamino-2,3-dihydrofuran;
2-phenyl-3-oxo-4-(5-methoxy-3-methoxycarbonylphenyl)-5-methylamino-2,3-dihydrofuran;
2-phenyl-3-oxo-4-(6-methyl-3-methoxycarbonylphenyl)-5-methylamino-2,3-dihydrofuran;
2-phenyl-3-oxo-4-(3-methoxycarbonyl-5-trifluoromethylphenyl)-5-methylamino-2,3-dihydrofuran;

2-phenyl-3-oxo-4-(3-methoxycarbonyl-5-fluorophenyl)-5-methylamino-2,3-dihydrofuran;
2-phenyl-3-oxo-4-(3-cyclopentyloxycarbonylphenyl)-5-methylamino-2,3-dihydrofuran;
2-(4-fluorophenyl)-3-oxo-4-(3-methoxycarbonylphenyl)-5-methylamino-2,3-dihydrofuran;
2-(1-naphthyl)-3-oxo-4-(3-methoxycarbonylphenyl)-5-methylamino-2,3-dihydrofuran;
2-phenyl-3-oxo-4-(2-chloro-3-phenoxycarbonylphenyl)-5-methylamino-2,3-dihydrofuran;
2-phenyl-3-oxo-4-(4-ethyl-3-2',6'-dimethylphenoxycarbonylphenyl)-5-methylamino-2,3-dihydrofuran;
2-phenyl-3-oxo-4-(5-methoxy-3-3',5'-dichlorophenoxycarbonylphenyl)-5-methylamino-2,3-dihydrofuran;
2-phenyl-3-oxo-4-(3-3'iodo-4'-methoxyphenoxycarbonylphenyl)-5-methylamino-2,3-dihydrofuran;
2-phenyl-3-oxo-4-(3-2'-nitro-4'-trifluoromethylphenoxycarbonylphenyl)-5-methylamino-2,3-dihydrofuran;
2-phenyl-3-oxo-4-(3-heptylthiocarbonylphenyl)-5-methylamino-2,3-dihydrofuran;
2-phenyl-3-oxo-4-(3,5-cyclohexyloxyphenyl)-5-methylamino-2,3-dihydrofuran;
2-(2-nitrophenyl)-3-oxo-4-(3-cyanophenyl)-5-methylamino-2,3-dihydrofuran;
2-phenyl-3-oxo-4-(2-chloro-3-nitrophenyl)-5-methylamino-2,3-dihydrofuran;
2-(1-naphthyl)-3-oxo-4-(3-ethylthiocarbonyl-2-ethylphenyl)-5-methylamino-2,3-dihydrofuran;
2-(1-naphthyl)-3-oxo-4-(3-dimethylcarbamoylphenyl)-5-methylamino-2,3-dihydrofuran;
2-phenyl-3-oxo-4-(3-carbamoylphenyl)-5-methylamino-2,3-dihydrofuran;
2-phenyl-3-oxo-4-(3-methylcarbamoylphenyl)-5-methylamino-2,3-dihydrofuran;
2-phenyl-3-oxo-4-(3-dioctylaminophenyl)-5-methylamino-2,3-dihydrofuran;
2-phenyl-3-oxo-4-(3-propylthiocarbonylphenyl)-5-methylamino-2,3-dihydrofuran;
2-phenyl-3-oxo-4-(3-2',5'-dimethoxycarbonylphenyl)-5-methylamino-2,3-dihydrofuran;
2-(3-nitrophenyl)-3-oxo-4-(3-3',4'-dibromophenoxycarbonylphenyl)-5-methylamino-2,3-dihydrofuran;
2-(2,3-dichlorophenyl)-3-oxo-4-(3-methoxycarbonylphenyl)-5-methylamino-2,3-dihydrofuran;
2-(1-naphthyl)-3-oxo-4-(3-ethoxycarbonylphenyl)-5-methylamino-2,3-dihydrofuran;
2-(3-chloro-8-fluoronaphth-1-yl)-3-oxo-4-(3-propoxycarbonylphenyl)-5-methylamino-2,3-dihydrofuran;
2-(2-trifluoromethyl-3-methyl-8-methoxy-naphth-1-yl)-3-oxo-4-(3-isopropoxycarbonylphenyl)-5-methylamino-2,3-dihydrofuran;
2-inden-1-yl-3-oxo-4-(3-butoxycarbonylphenyl)-5-methylamino-2,3-dihydrofuran; and
2-(2-fluoroinden-1-yl)-3-oxo-4-(3-hexoxycarbonylphenyl)-5-methylamino-2,3-dihydrofuran; and
2-(3-methoxy-5-nitro-7-fluoromethylnaphth-1-yl)-3-oxo-4-(3-ethylcarbamoylphenyl)-5-methylamino-2,3-dihydrofuran;
2-(3-chlorophenyl)-3-oxo-4-(2-trifluoromethyl-3-dimethylcarbamoylphenyl)-5-methylamino-2,3-dihydrofuran;
2-naphth-1-yl-3-oxo-4-(5-trifluoromethyl-3-ethylthiocarbonylphenyl)-5-methylamino-2,3-dihydrofuran;
2-(3-methylphenyl)-3-oxo-4-(3-butoxycarbonyl-4-methylphenyl)-3-oxo-5-methylamino-2,3-dihydrofuran;
2-(3-fluorophenyl)-3-oxo-4-(3-3'-chlorophenoxycarbonylphenyl)-5-methylamino-2,3-dihydrofuran;
2-(2,3,5-trifluorophenyl)-3-oxo-4-(3-phenoxycarbonylphenyl)-5-methylamino-2,3-dihydrofuran;
2-(3-methylnapth-1-yl)-3-oxo-4-(3-methoxycarbonylphenyl)-5-methylamino-2,3-dihydrofuran;
2-(2-nitro-3-methoxyphenyl)-3-oxo-4-(3-phenoxycarbonylphenyl)-5-methylamino-2,3-dihydrofuran.

Similarly, by approximately doubling the amount of dimethylsulfate and increasing the reaction time, the corresponding 5-dimethylamino homologs of the above compounds can be prepared. Similarly, by using diethylsulfate in place of dimethylsulphate the corresponding 5-ethylamino and 5-diethylamino homologs of the above compounds can be prepared.

EXAMPLE 4

2-(2-Fluorophenyl)-3-oxo-4-(3-methoxycarbonylphenyl)-5-allylamino-2,3-dihydrofuran The title compound can be prepared via the following procedure.

One gram of sodium hydroxide in 4.0 ml of water is added to a mixture of 4.0 g of 2-(2-fluorophenyl)-3-oxo-4-(3-methoxycarbonylphenyl)-5-methylamino-2,3-dihydrofuran in 80 ml of methylene chloride at room temperature followed by the addition of 1.48 g of allyl bromide and 0.27 g of benzyltriethylammonium chloride. This will result in a two-phase mixture. This mixture is stirred at room temperature for about 18 hours and this is washed with water, dried over magnesium sulfate and concentrated in vacuo. The residue is purified by chromatography over silica gel eluting with chloroform to yield the title compound.

Similarly, by applying this procedure to the products listed in Example 2, the corresponding 5-allylamino analogs thereof can be prepared. Similarly, by approximately doubling the amount of allyl bromide and sodium hydroxide, the corresponding 5-diallylamino analogs thereof can be prepared.

In a like manner, by using ethyl bromide in place of allyl bromide, the corresponding 5-ethylamino and 5-diethylamino analogs can be prepared.

Similarly, by following the same procedure by respectively using methoxymethyl bromide, ethylthiomethyl bromide, methyl bromoacetate, methyl 2-bromobutyrate, 1,5-dibromopentane, and cis-1,4-dibromobut-1,3-diene in place of alkyl bromide the corresponding 5-methoxymethylamino, 5-ethylthiomethylamino, 5-methoxycarbonylmethylamino, 5-(1-methoxycarbonylpropylamino), 5-piperidin-1-yl and 5-pyrrol-1-yl analogs of the products listed in Example 2 can be prepared for example:
2-phenyl-3-oxo-4-(3-methoxycarbonylphenyl)-5-methoxycarbonylamino-2,3-dihydrofuran;
2-phenyl-3-oxo-4-(3-2',6'-dimethylphenoxylcarbonylphenyl)-5-methoxycarbonylmethylamino-2,3-dihydrofuran;
2-phenyl-3-oxo-4-(3-ethylthiocarbonylphenyl)-5-(1-methoxycarbonylprop-1-yl)amino-2,3-dihydrofuran;
2-naphth-1-yl-3-oxo-4-(3-cyclohexylcarbonylphenyl)-5-(1-methoxycarbonylprop-1-yl)amino-2,3-dihydrofuran;
2-inden-1-yl-3-oxo-4-(3-propylthiocarbonylphenyl)-5-(1-methoxycarbonylprop-1-yl)amino-2,3-dihydrofuran,
2-phenyl-3-oxo-4-(3-pentoxycarbonylphenyl)-5-piperidin-1-yl-2,3-dihydrofuran; and
2-phenyl-3-oxo-4-(3-cyanophenyl)-5-pyrrol-1-yl-2,3-dihydrofuran, etc.

Similarly, by applying the above procedures using the 5-methylamino products of Example 4 as starting materials, the corresponding 5-(N-methyl-N-allylamino), 5-(N-methyl-N-ethylamino), 5-(N-methyl-N-methoxymethylamino), 5-(N-methyl-N-ethylthiomethylamino), 5-(N-methyl-N-methoxycarbonylmethylamino), and 5-(N-methyl-N-1'-methoxycarbonylpropylamino) analogs can be prepared.

EXAMPLE 5

Lithium salt of 2-phenyl-3-oxo-4-(3-methoxycarbonylphenyl)-5-methylamino-2,3-dihydrofuran ($R^1$=—$CH_3$, $R^2$=Li)

This example illustrates a procedure for preparing the title compound.

In this example, 5.5 ml of 1.6M n-butyllithium in hexane is added dropwise to a stirred solution containing 2.86 g of 2-phenyl-3-oxo-4-(3-methoxycarbonylphenyl)-5-amino-2,3-dihydrofuran in 25 ml of tetrahydrofuran at −30° C. The resulting mixture is stirred for about 20 minutes and then concentrated in vacuo to afford a residue of the title compound.

Similarly, by adapting the above procedure, the corresponding lithium salts of the other compounds of Example 2 can also be prepared.

Example 6

The compounds listed in Table A hereinbelow were prepared using the appropriate starting materials and the appropriate procedures described in the Examples hereinabove.

TABLE A

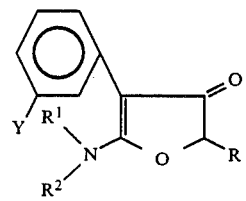

| | | | | | ELEMENTAL ANALYSIS | | | | | | Melting |
| | | | | | Carbon | | Hydrogen | | Nitrogen | | Point |
| No. | $R^1$ | $R^2$ | R | Y | Calc. | Found | Calc. | Found | Calc. | Found | °C. |
|---|---|---|---|---|---|---|---|---|---|---|---|
| *1(I) | H | H | φ | $CH_3OOC$— | 73.72 | 73.01 | 5.12 | 5.77 | 4.78 | 5.49 | 83–84 |
| 2 | H | $CH_3$ | φ | $CH_3OOC$— | 70.59 | 70.42 | 5.26 | 6.05 | 4.33 | 4.51 | 179–184** dec |
| 3(I) | H | H | φ | $CH_3CH_2OOC$— | 70.59 | 69.31 | 5.26 | 5.57 | 4.33 | 4.94 | 170–173 dec |
| 4 | H | $CH_3$ | φ | $CH_3CH_2OOC$— | 71.22 | 70.07 | 5.64 | 5.85 | 4.15 | 5.32 | 173–175 dec |

*The suffix (I) refers to intermediates
**dec = Decomposition

TABLE B

COMPARISON COMPOUNDS

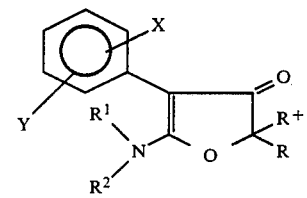

(unless otherwise noted X = H and $R^+$ = H)

| | | | | | ELEMENTAL ANALYSIS | | | | | | Melting |
| | | | | | Carbon | | Hydrogen | | Nitrogen | | Point |
| No. | $R^1$ | $R^2$ | R | Y | Calc. | Found | Calc. | Found | Calc. | Found | °C. |
|---|---|---|---|---|---|---|---|---|---|---|---|
| C-1 | $CH_3$ | $CH_3$ | φ | H | 77.42 | 75.64 | 6.09 | 6.39 | 5.02 | 5.03 | 111–115 |
| C-2 | H | H | H | H | 68.57 | 68.99 | 5.14 | 5.78 | 8.0 | 7.87 | 221–223* |
| C-3 | H | H | H | 3-Cl | 57.29 | 51.6 | 6.68 | 5.67 | 3.82 | 3.7 | 214–216* |
| C-4 | H | H | H | 4-Cl | 57.29 | 53.46 | 6.68 | 5.52 | 3.82 | 4.11 | 169–170* |
| C-5 | $CH_3$ | H | H | 4-Cl | 59.07 | 59.34 | 4.48 | 5.03 | 6.27 | 6.02 | 133–137* |
| C-6 | $CH_3$ | $CH_3$ | H | 4-Cl | 60.64 | 58.61 | 5.05 | 5.24 | 5.90 | 5.76 | 161–163 |
| C-7 | $CH_3$ | H | φ | 4-Cl | 68.1 | 64.4 | 4.7 | 5.3 | 4.7 | 4.5 | oil |
| C-8 | H | H | H | 4-$CH_3$ | 69.84 | 67.98 | 5.82 | 5.63 | 7.41 | 6.7 | 189–191* |
| C-9 | $CH_3$ | H | H | 4-$CH_3$ | 70.94 | 70.85 | 6.4 | 6.63 | 6.9 | 6.96 | 151–156* |
| C-10 | H | H | φ | 4-$CH_3$ | 77.0 | 76.2 | 5.7 | 5.9 | 5.3 | 5.05 | 142–146 |
| C-11 | $CH_3$ | H | φ | 4-$CH_3$ | 77.4 | 75.49 | 6.1 | 6.14 | 5.0 | 4.89 | 148–154 |
| C-12 | H | H | φ | 4-$OCH_3$ | 72.6 | 70.5 | 5.4 | 6.0 | 5.0 | 4.8 | 138–141 |
| C-13 | $CH_3$ | $CH_3$ | φ | 4-$OCH_3$ | 73.8 | 72.9 | 6.2 | 6.7 | 4.5 | 4.7 | 140–143 |
| C-14 | ** | H | φ | 3-$CF_3$ | 62.7 | 62.4 | 3.4 | 4.5 | 5.8 | 5.8 | oil |
| C-15 | $CH_3$ | $CH_3$ | R = φ, $R^+$ = Cl | 3-$CF_3$ | 59.76 | 57.9 | 3.93 | 4.06 | 3.67 | 3.56 | oil |

TABLE B-continued
COMPARISON COMPOUNDS

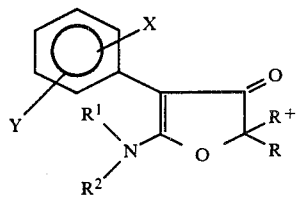

(unless otherwise noted X = H and R+ = H)

| No. | R¹ | R² | R | Y | ELEMENTAL ANALYSIS | | | | | | Melting Point °C. |
|---|---|---|---|---|---|---|---|---|---|---|---|
| | | | | | Carbon | | Hydrogen | | Nitrogen | | |
| | | | | | Calc. | Found | Calc. | Found | Calc. | Found | |
| C-16[2] | H | H | φ | Y = 3-Cl, X = 4-Cl | 60.0 | 60.1 | 3.5 | 3.7 | 4.4 | 4.8 | 179–182 |

C-16[2] is 2-phenyl-3-oxo-4-(3,4-dichlorophenyl)-5-amino-2,3-dihydrofuran
*Decomposition
**4-NO₂φ—

Example 7

In this example, the compounds of Example 6 were respectively tested using the procedures described hereinbelow for pre-emergent and post-emergent activity against a variety of grasses and broad-leaf plants including one grain crop and one broad-leaf crop. The compounds tested are identified by compound number in Tables given in Example 6 hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm² or in some instances as indicated in Table 1 hereinbelow, certain of the compounds were tested at a lower dosage of 15.6 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1
Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 0 | 0 | 0 | 0 | 0 | 0 | 0 | 0 |
| 2 | 90 | 100 | 95 | 30 | 100 | 100 | 100 | 90 |
| 3 | 0 | 0 | 0 | 0 | 0 | 0 | 0 | 0 |
| 4 | 100 | 100 | 100 | 60 | 100 | 100 | 95 | 70 |
| 5 | — | — | — | — | — | — | — | — |
| 6 | — | — | — | — | — | — | — | — |
| 7 | — | — | — | — | — | — | — | — |
| 8 | — | — | — | — | — | — | — | — |
| 9 | — | — | — | — | — | — | — | — |
| 10 | — | — | — | — | — | — | — | — |
| 11 | — | — | — | — | — | — | — | — |
| 12 | — | — | — | — | — | — | — | — |
| 13 | — | — | — | — | — | — | — | — |
| 14 | — | — | — | — | — | — | — | — |
| 15 | — | — | — | — | — | — | — | — |
| 16 | — | — | — | — | — | — | — | — |
| 17 | — | — | — | — | — | — | — | — |

TABLE 1-continued

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 18 | — | — | — | — | — | — | — | — |
| 19 | — | — | — | — | — | — | — | — |
| 20 | — | — | — | — | — | — | — | — |
| 21 | — | — | — | — | — | — | — | — |
| 22 | — | — | — | — | — | — | — | — |
| 23 | — | — | — | — | — | — | — | — |
| 24 | — | — | — | — | — | — | — | — |
| 25 | — | — | — | — | — | — | — | — |
| 26 | — | — | — | — | — | — | — | — |

TABLE 1A

COMPARISON COMPOUNDS
Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-1 | 40 | 25 | 40 | 0 | 75 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 30 | 25 | 0 | 40 | 0 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 30 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14 | 0 | 0 | 0 | 0 | 45 | 35 | 0 | 0 |
| C-15 | 0 | 0 | 0 | 0 | 0 | 0 | 0 | 0 |
| C-16 | 0 | 0 | 0 | 0 | 0 | 0 | 0 | 0 |

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| 1 | 0 | 0 | 0 | 0 | 0 | 0 | 0 | 0 |
| 2 | 20 | 60 | 35 | 10 | 35 | 10 | 25 | 0 |
| 3 | 0 | 0 | 0 | 0 | 0 | 0 | 0 | 0 |
| 4 | 30 | 30 | 30 | 30 | 0 | 0 | 0 | 0 |

TABLE 2A

COMPARISON COMPOUNDS
Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-1 | 20 | 20 | 0 | 25 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 25 | 20 | 25 | 30 | 0 | 0 | 0 | 0 |
| C-9 | 20 | 20 | 10 | 25 | 0 | 0 | 0 | 0 |
| C-10 | 0 | 0 | 0 | 0 | 0 | 0 | 0 | 0 |
| C-11 | 20 | 0 | 0 | 20 | 0 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14 | 0 | 0 | 0 | 0 | 0 | 0 | 0 | 0 |
| C-15 | 25 | 25 | 0 | 30 | 25 | 10 | 45 | 45 |

TABLE 2A-continued
COMPARISON COMPOUNDS
Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambsquarter | Mustard | Pigweed | Soybean | Crabgrass | Watergrass | Wild Oats | Rice |
| C-16 | 0 | 0 | 0 | 0 | 0 | 0 | 0 | 0 |

As can be seen from the above tables, Compound Nos. 2 and 4 exhibited excellent pre-emergence activity and modest or weak post-emergence activity. In contrast to this the corresponding des-methyl intermediates were wholly inactive as were also most of the comparison compounds.

Obviously, many modifications and variations of the invention described hereinabove and below can be made without departing from the essence and scope thereof.

What is claimed is:

1. A compound having the formula:

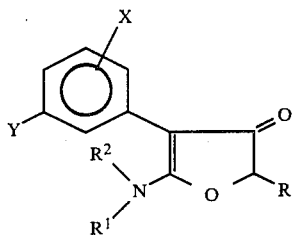

(I)

wherein
R is phenyl, naphth-1-yl, inden-1-yl; 4-fluorophenyl; or R is a substituted aryl selected from the group having the formulas:

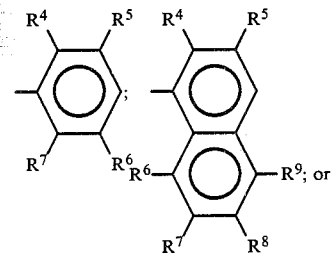

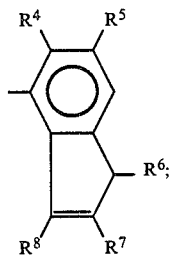

wherein
one, two or three of R⁴, R⁵, R⁶, R⁷, R⁸, and R⁹ are independently selected from the group of lower alkyl, lower alkoxy, halo, nitro, or haloalkyl having 1 through 3 carbon atoms and 1 through 3 of the same or different halo atoms, and the remainder are hydrogen;

R¹ is hydrogen or alkyl having 1 through 4 carbon atoms;

R² is hydrogen, alkyl having 1 through 4 carbon atoms, alkenyl having 3 or 4 carbon atoms, lower alkoxycarbonylalkyl, lower alkoxyalkyl or lower alkylthioalkyl;

R¹ and R² together with the nitrogen atom to which they are joined form a saturated or unsaturated nitrogen heterocycle having 5 or 6 ring atoms one of which is nitrogen and the remainder are carbon atoms;

X is hydrogen, lower alkyl, lower alkoxy, halo, or trifluoromethyl and can be at any available position on the phenyl ring; and Y is cyano; nitro; alkoxycarbonyl having 2 through 9 carbon atoms; cyclopentyloxycarbonyl; cyclohexyloxycarbonyl; phenoxycarbonyl; substituted phenoxycarbonyl having 1 or 2 substituents independently selected from the group of lower alkyl having 1 through 6 carbon atoms, lower alkoxy having 1 through 6 carbon atoms, halo, haloalkyl having 1 through 3 carbon atoms and 1 through 4 of the same or different halo atoms, nitro or cyano; alkylthiocarbonyl having 2 through 9 carbon atoms, or

wherein R¹⁰ and R¹¹ are independently hydrogen or alkyl having 1 through 8 carbon atoms; and compatible salts thereof.

2. The compound of claim 1 wherein one of R¹ or R² is hydrogen, methyl, ethyl or propyl.

3. The compound of claim 1 wherein one of R¹ or R² is methyl or ethyl and the other is hydrogen, methyl or ethyl.

4. The compound of claim 1 wherein one of R¹ or R² is hydrogen and the other is methyl, ethyl or propyl.

5. The compound of claim 1 wherein X is hydrogen.

6. The compound of claim 2 wherein X is hydrogen.

7. The compound of claim 3 wherein X is hydrogen.

8. The compound of claim 1 wherein R is phenyl, naphth-1-yl, 4-fluorophenyl or substituted aryl.

9. The compound of claim 8 wherein R is phenyl, naphthyl or a monosubstituted phenyl.

10. The compound of claim 9 wherein R is phenyl, halophenyl, or lower alkylphenyl.

11. The compound of claim 10 wherein R is phenyl, 4-fluorophenyl, 2-halophenyl, or 2-lower alkylphenyl.

12. The compound of claim 11 wherein X is hydrogen and R¹ and R² are independently selected from the group of hydrogen, methyl or ethyl.

13. A compound having the formula:

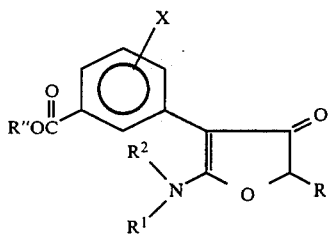

(I)

wherein

R is phenyl, naphth-1-yl, inden-1-yl; 4-fluorophenyl; or R is a substituted aryl selected from the group having the formulas:

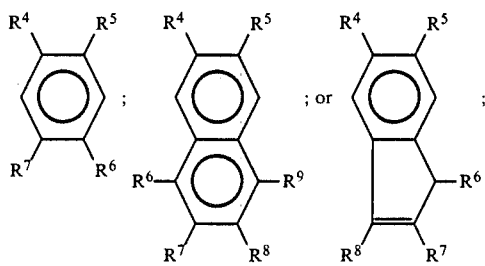

wherein one, two or three of $R^4$, $R^5$, $R^6$, $R^7$, $R^8$, and $R^9$ are independently selected from the group of lower alkyl, lower alkoxy, halo, nitro, or haloalkyl having 1 through 3 carbon atoms and 1 through 3 of the same or different halo atoms, and the remainder are hydrogen;

$R^1$ is hydrogen or alkyl having 1 through 4 carbon atoms;

$R^2$ is hydrogen, alkyl having 1 through 4 carbon atoms, alkenyl having 3 or 4 carbon atoms, lower alkoxycarbonylalkyl, lower alkoxyalkyl or lower alkylthioalkyl;

$R^1$ and $R^2$ together with the nitrogen atom to which they are joined form a saturated or unsaturated nitrogen heterocycle having 4 through 6 ring atoms one of which is nitrogen and the remainder are carbon atoms;

X is hydrogen, lower alkyl, lower alkoxy, halo, or trifluoromethyl and can be at any available position on the phenyl ring; and R" is alkyl having 1 through 7 carbon atoms; and compatible salts thereof.

14. The compound of claim 13 wherein $R^1$ and $R^2$ are independently hydrogen, methyl or ethyl.

15. The compound claim 14 wherein one of $R^1$ or $R^2$ is methyl or ethyl and the other is hydrogen, methyl or ethyl.

16. The compound of claim 13 wherein one of $R^1$ or $R^2$ is methyl or ethyl and the other is hydrogen.

17. The compound of claim 14 wherein X is hydrogen and R is phenyl, naphthyl, 4-fluorophenyl, 2-halophenyl or 2-lower alkylphenyl.

18. The compound of claim 17 wherein one of $R^1$ or $R^2$ is hydrogen and the other is hydrogen methyl or ethyl.

19. The compound of claim 18 wherein R is phenyl, 2-fluorophenyl 2-chlorophenyl or 2-methylphenyl.

20. The compound of claim 18 wherein R is phenyl.

21. The compound of claim 18 wherein R is phenyl and one of $R^1$ or $R^2$ is hydrogen and the other is methyl.

22. The compound of claim 18 wherein R is phenyl and one of $R^1$ or $R^2$ is hydrogen and the other is ethyl.

23. The compound of claim 13 wherein X is hydrogen.

24. The compound of claim 5 wherein Y is a lower haloalkyl having 1 or 2 carbon atoms.

25. A herbicidal composition comprising a herbicidally effective amount of a compound according to claim 1, or mixtures of such compounds, and a compatible carrier.

26. A herbicidal composition comprising a herbicidally effective amount of a compound according to claim 20, or mixtures thereof, and a compatible carrier.

27. A method for controlling plants which comprises applying a herbicidally effective amount of a compound according to claim 1, or mixtures thereof, to the foliage or potential growth medium of said plants.

28. A method for controlling plants which comprises applying a herbicidally effective amount of a compound according to claim 20, or mixtures thereof, to the foliage or potential growth medium of said plants.

29. A method for regulating the growth of plants which comprises applying to the foliage of said plants or their growth medium an amount of a compound according to claim 1, or mixtures thereof, effective to alter the growth pattern of such plants.

* * * * *